United States Patent
Nolens et al.

(10) Patent No.: US 11,413,138 B2
(45) Date of Patent: Aug. 16, 2022

(54) NASAL IMPLANT

(71) Applicant: CERHUM SA, Liège (BE)

(72) Inventors: Grégory Nolens, Liège (BE); Charles Wolf, Braine l'Alleud (BE); Giancarlo Cantella, Brussels (BE); Thibaut Breuls De Tiecken, Hotton (BE)

(73) Assignee: CERHUM SA, Liège (BE)

( * ) Notice: Subject to any disclaimer, the term of this patent is extended or adjusted under 35 U.S.C. 154(b) by 14 days.

(21) Appl. No.: 16/495,052

(22) PCT Filed: Mar. 16, 2018

(86) PCT No.: PCT/EP2018/056724
§ 371 (c)(1),
(2) Date: Sep. 17, 2019

(87) PCT Pub. No.: WO2018/167292
PCT Pub. Date: Sep. 20, 2018

(65) Prior Publication Data
US 2020/0155304 A1     May 21, 2020

(30) Foreign Application Priority Data
Mar. 17, 2017   (BE) .................................. 2017/5168

(51) Int. Cl.
*A61F 2/18*     (2006.01)
*B33Y 10/00*    (2015.01)
(Continued)

(52) U.S. Cl.
CPC ........ *A61F 2/186* (2013.01); *A61F 2240/001* (2013.01); *A61F 2310/00293* (2013.01);
(Continued)

(58) Field of Classification Search
CPC ...... A61F 2/186; A61F 2/18; A61F 2240/001; A61F 2310/00293; A61F 2/0059;
(Continued)

(56) References Cited

U.S. PATENT DOCUMENTS 6,277,150 B1 *  8/2001  Crawley ................. A61L 27/16
                                                  623/17.18
6,811,570 B1 * 11/2004  Gehl ....................... A61L 27/58
                                                  623/23.75
(Continued)

FOREIGN PATENT DOCUMENTS

EP    2 320 966 A1     5/2011
KR    10-1505385 B1    3/2015
(Continued)

OTHER PUBLICATIONS

Database WPI Thomson Scientific, London, GB; vol. 2015, No. 25, AN 2015-22995T0 XP002776250.
(Continued)

*Primary Examiner* — Brian A Dukert
*Assistant Examiner* — Rebecca Lynee Zimmerman
(74) *Attorney, Agent, or Firm* — Lewis Roca Rothgerber Christie LLP (57) ABSTRACT

Nasal implant obtained by additive manufacturing, comprising a main portion and a return portion connected by an intermediate portion, the main and return portions forming an angle of between 25° and 90°,
  said implant is made from a biocompatible ceramic of synthetic origin;
  said implant has an average macroporosity characterized by:
    a density of material of between 20% and 95% by volume, said density of material being higher in said intermediate portion than in said main portion;
(Continued)

cavities defining sections of cavities, said sections of cavities each having a diameter of between 0.3 mm and 1 mm;

said sections of cavities each having an area and a form substantially equal over the entire implant.

15 Claims, 4 Drawing Sheets

(51) Int. Cl.
*B33Y 50/02* (2015.01)
*B33Y 70/00* (2020.01)
*B33Y 80/00* (2015.01)

(52) U.S. Cl.
CPC ............... *B33Y 10/00* (2014.12); *B33Y 50/02* (2014.12); *B33Y 70/00* (2014.12); *B33Y 80/00* (2014.12)

(58) Field of Classification Search
CPC ....... A61F 2240/002; A61F 2210/0004; B33Y 10/00; B33Y 50/02; B33Y 70/00; B33Y 80/00; A61L 27/56; A61L 27/12; A61L 27/10; A61L 27/58
See application file for complete search history.

(56) References Cited

U.S. PATENT DOCUMENTS

| | | | |
|---|---|---|---|
| 2004/0019389 A1* | 1/2004 | Swords | A61F 2/2803 623/23.72 |
| 2005/0002911 A1 | 1/2005 | Kanemaru et al. | |
| 2010/0023130 A1* | 1/2010 | Henry | A61L 27/48 623/17.18 |
| 2015/0012090 A1 | 1/2015 | Saidi | |
| 2017/0333190 A1* | 11/2017 | Vickers | A61K 6/838 |
| 2018/0168802 A1* | 6/2018 | Wu | A61F 2/186 |

FOREIGN PATENT DOCUMENTS

| | | | |
|---|---|---|---|
| KR | 10-2016-0024894 A1 | | 3/2016 |
| WO | WO 2004/009000 A1 | | 1/2004 |

OTHER PUBLICATIONS

Database WPI Thomson Scientific, London, GB; vol. 2016, No. 24, AN 2016-17152N0 XP002776251.

International Search Report and Written Opinion for PCT Patent Application No. PCT/EP2018/056724, dated Jun. 19, 2018 (9 sheets).

* cited by examiner

NASAL IMPLANT

CROSS-REFERENCE TO RELATED APPLICATIONS

This application is a National Phase Patent Application of International Patent Application Number PCT/EP2018/056724, filed on Mar. 16, 2018, which claims priority to and benefit of Belgium Patent Application Number 2017/5168, filed on Mar. 17, 2017, the entire contents of each of which are incorporated herein by reference.

TECHNICAL FIELD

According to a first aspect, the invention relates to a nasal implant.

According to a second aspect, the invention relates to a method for manufacturing a nasal implant.

PRIOR ART

A nasal implant is intended to be implanted in the nose of an individual during plastic or restorative surgery, in order to modify the external appearance of the nose of an individual. A nasal implant is implanted under the skin and requires to be produced with biocompatible materials in order to prevent rejection reactions.

Biocompatible materials used for producing nasal implants may come from the individual in which the implant is intended to be implanted, that is to say after taking and shaping fragments of bone or cartilage for example. Materials of animal origin may also be used, they require for example to be formed by mechanical and chemical methods. Biocompatible metal, plastic or ceramic materials may also be used.

A biocompatible implant affords good compatibility with the organism in which it is implanted so that the organism does not reject it. However, biocompatible materials may have drawbacks in the longer or shorter term because of the formation of scar tissue and/or inflammatory reaction to a foreign body around these implants, which may then require further surgery. To overcome this drawback, the biocompatible materials may also be bioresorbable, that is to say they may be assimilated by the organism in order to leave space for a tissue or cartilage.

The document EP 2 320 966 A1 describes a nasal implant manufactured from a tendon of animal origin treated and shaped in order to form such an implant.

Compounds of animal origin are less and less desirable for producing implants although they have high biocompatibility. Non-autograft compounds of animal or human origin are less and less desirable in general terms because of the risk of contamination of which they may be the cause.

The document US 2015/0012090 A1 describes a method for deploying a nasal implant in a nose by means of an injection device. The implant being able to be manufactured from metal, polymers or ceramic matrices. For example, such an implant produced from porous polyethylene allows fibrovascularisation thereof. One disadvantage of this type of implant is that it does not make it possible to have a bioresorbable implant having bioresorbability that can be controlled, having macroporosity for which the diameter of the pores is controlled.

SUMMARY OF THE INVENTION

According to a first aspect, one of the aims of the invention is to provide an at least partially biointegratable and potentially bioresorbable nasal implant without having recourse to compounds of animal origin. Another aim of the invention is to provide an implant having macroporosity wherein the diameter of the pores and the distribution of the pores in the implant are well controlled. To this end the inventors propose, according to a first aspect, a nasal implant obtained by additive manufacturing, comprising:
- a main portion,
- a return portion, and
- an intermediate portion;
- said main portion and said return portion being connected by said intermediate portion;
- said main portion and return portion forming an angle of between 25° and 90°,
- characterised in that:
- said implant is made from a biocompatible ceramic of synthetic origin;
- said implant has an average macroporosity characterised by:
  - a density of material of between 20% and 95% by volume, said density of material being higher in said intermediate portion than in said main portion;
  - cavities at least partially delimited by lateral walls defining sections of cavities, said sections of cavities each having an extension such that it is possible to inscribe each of said sections of cavities in a circle having a diameter of between 0.3 mm and 1 mm;
- said sections of cavities each having an area and a form substantially equal over the entire implant.

The invention makes it possible to have a biocompatible, biointegratable and potentially bioresorbable implant having high rigidity and which allows rapid colonisation by the tissue in which it is implanted. The invention makes it possible to have an implant having the advantages of a ceramic implant with the advantage of a biointegratable and potentially bioresorbable implant. The invention makes it possible to have a synthetic implant. The invention makes it possible to have an implant having macroporosity allowing rapid growth of the tissues in order to afford good holding of the implant in the tissue in which it is implanted.

The advantage of a nasal implant having macroporosity wherein the diameter of the pores and the distribution of the pores are well controlled is to allow more homogeneous and quicker resorption of the implant. This also allows regeneration of the tissues or cartilages that is more homogeneous and quicker. This also makes it possible to obtain more satisfactory results following implantation of the implant of the invention.

A biocompatible ceramic of synthetic origin is for example manufactured by chemical synthesis methods.

The invention makes it possible to very greatly reduce the risks of contamination compared with the use of an implant of animal or human origin coming from another donor.

The nasal implant comprising a main portion, as well as any return portion and any intermediate portion, after implantation in the nose of an individual, enables the latter to have a nose having a profile close to that of the implant claimed. The connection between the main portion, the return portion and the intermediate portion makes it possible to have a rigid assembly that is non-deformable, both at the time of implantation and in the days following the implantation. The angle formed between the main portion and the return portion makes it possible to adapt the shape of the implant to the nose profile sought by the patient.

The advantage of the invention compared with a kit prosthesis or cuttable prosthesis is to be able to have a made-to-measure prosthesis not requiring any adaptation when fitting. The invention therefore allows rapid fitting and makes it possible to have a prosthesis adapted to the patient.

A prosthesis or implant adapted to the patient is a personalisable implant making it possible to match the anatomical forms of the patient as well as being able to define a chosen shape of the nose in which it is implanted. Such a personalisable implant has the advantage of being able to perfectly make up for any defect. Such an implant makes it possible to be fixed better to the patient by increasing the surface areas of contact with the tissues present by virtue of the control of the porosities.

The implant of the invention is obtained by additive manufacturing and preferentially by three-dimensional printing. This manufacturing method makes it possible to obtain macroporosity that is controlled, that is to say well proportioned/distributed in the implant, with cavities having quite regular uniform cross-sections. In addition, this manufacturing method allows control of the microporosity of the implant as well as of the roughness of the external walls and/or of the walls delimiting the cavities. Additive manufacturing allows excellent control of the macroporosity as well as of the overall shape of the implant without having to have recourse to machining of the implant after it is manufactured. Typically, control of the macroporosity that is allowed by additive manufacturing cannot be obtained by an injection method or by a conventional machining method. An injection method is for example a method where the macroporosity is formed by a sacrificial material that is removed after solidification of the matrix of the implant around the sacrificial material, then leaving a porous material.

The porosity of the implant is preferably uniform, that is to say it is characterized by a single form. For example, uniform means that the cavities having a given cavity cross-section are distributed regularly in the implant and that said cavity cross-sections are controlled for size. The controlled cavity cross-sections have predefined and preferably equal cavity cross-sections. The porosity is preferably homogeneous, that is to say, for a defined volume and zone and for a plurality of defined volumes and zones, the porosity is distributed homogeneously in the volume. Preferably the porosity is defined by a distribution of the pores periodically for a given zone or volume. Preferably the porosity of the implant is connected, that is to say there exists a possible route between the porosities without passing outside the implant.

Said cavity cross-sections each having an area and form that are substantially equal over the entire implant, for example if the cross-section is a given polygon, then the same type of polygon is kept in the entire implant. For example, the cavity cross-sections have circular or elliptical shapes.

The intermediate portion may be called the point portion or point. The main portion is preferably intended to be substituted for or to reinforce the growth intermediate to the cartilage of the nose (the nasal dorsum) or to the septal cartilage of the nose. The return portion is preferably intended to be positioned at the columella of the nose.

Preferably, the nasal implant of the invention is designed so that it is not porous or having a high density at the parts that would be in contact with the dura mater or with a membrane. On the other hand the implant is designed so that it has maximum porosity in contact with a bone or with a cartilage. Such a distribution of the macroporosity according to the anatomical nature of the part with which the implant is in contact affords better regeneration of the implant, that is to say high bioresorbability at the bone or cartilage thus allowing solidification/rigidification of the bone or cartilage in contact.

The nasal implant proposed by the invention is a nose prosthesis.

In addition to the biocompatible and potentially bioresorbable character of the materials used for manufacturing a nasal implant, the invention makes it possible to have an implant having macroporosity. The macroporosity enables the tissues to grow in the cavities characterizing the macroporosity. The macroporosity makes it possible to have a lighter nasal implant while keeping its shape and rigidity compared with a nasal implant with the same appearance but without macroporosity.

Macroporosity designates a porosity wherein the smallest dimension is preferably greater than 100 μM, even more preferably greater than 200 μM. Macroporosity may be defined by a density of material corresponding to a ratio of the volume of the pores to the total volume of the object. The pores are also cavities, holes or orifices.

The advantage of being able to vary the average macroporosity of the nasal implant is being able to have a nasal implant having a variable macroporosity volume, a variable macroporosity diameter or a variable number of pores.

Average macroporosity of the nasal implant means that an average macroporosity value is designated in the whole of the nasal implant. Average macroporosity corresponds for example to the integration of the macroporosity of the main, intermediate and return portions over the whole of the volume of these portions or of the nasal implant. For example, the portions may have different macroporosity values, an average macroporosity value corresponds to a weighted average of the macroporosities of each of the portions.

The angle defined between the main and return portions corresponds for example to the angle measured between an axis representing the orientation of the main portion and an axis representing the orientation of the return portion.

The cavities are defined by lateral walls, the cavities are defined by cross-sections taken perpendicular to the lateral walls. For example, in the case of a cylindrical cavity the cross-section corresponds to the diameter of a circle taken perpendicular to the tangent to the lateral wall. Preferably, in the case of a non-cylindrical cavity, the cross-section is defined by a circle. The circle defining the cross-section has a diameter making it possible to inscribe the cross-section, the diameter of the circle defining the cross-section of a cavity is preferably between 0.3 mm and 1 mm. The cavities are preferably not parallel to each other. For example, the cavities have cross-sections of variable diameters. For example, a cavity comprises a plurality of cross-sections with diameters of between 0.3 mm and 1 mm.

The invention has a macroporosity that, compared with microporosity, allows good population of the implant of the invention by cells of the host body, affording good bioresorbability of the implant in the host body.

Preferably, the biocompatible ceramic comprises a synthetic bioceramic.

Bioceramics are ceramics used as biomaterials for producing implants or a prosthesis for example as defined by the reference work Biomechanics and Biomaterials in Orthopaedics, T. Yamamuro. Bioceramics of synthetic origin are for example obtained by chemical and/or physical methods. Synthetic bioceramics are preferably composed of synthetic raw materials. For example, synthetic bioceramics are manufactured by chemical synthesis methods. For example, synthetic bioceramics are manufactured by physical synthesis methods. For example, synthetic bioceramics are manufactured by chemical and physical synthesis methods. For example, bioceramics of synthetic origin do not come directly from materials of animal or plant origin. For example, bioceramics of synthetic origin comprise natural and synthetic raw materials and additives that are used by industrial processes.

The bioceramics are biocompatible. Preferably, the bioceramics are bioresorbable.

Preferably, the biocompatible ceramic comprises a bioglass. The bioglasses are biocompatible. Preferably the bioglasses are bioresorbable.

Preferably, the nasal implant further comprises a return portion and an intermediate portion; said main portion and said return portion being connected by said intermediate portion; said main portion and return portion forming an angle of between 25° and 90°.

Preferably, the biocompatible ceramic comprises a bioceramic composition lying between 0 and 100% and a bioglass composition lying between 0 and 100%.

Preferably, the biocompatible ceramic comprises a calcium phosphate composition lying between 0 and 100%.

Preferably, the biocompatible ceramic comprises a hydroxyapatite composition lying between 0 and 100% and more preferentially between 10% and 60% and even more preferentially between 25% and 45%.

Preferably, the biocompatible ceramic comprises a tricalcium phosphate composition lying between 0 and 100% and more preferentially between 40% and 90% and even more preferentially between 55% and 75%.

The invention makes it possible to have an implant composed of elements naturally present in the human body, such as for example calcium phosphates or for example hydroxyapatite and tricalcium phosphate.

The tricalcium phosphate and hydroxyapatite compositions preferably comprise respectively between 0 and 100% and between 0% and 100%, more preferentially their compositions are respectively between 20% and 100% and between 0 and 80%, even more preferentially their compositions are respectively between 40% and 90% and between 10% and 60%.

The composition of the implant made from hydroxyapatite and tricalcium phosphate affords good biocompatibility of the implant with the body of a receiving individual. Hydroxyapatite and tricalcium phosphate are naturally present in the human body and more particularly in the bone matrix of the bones. This composition also affords bioresorbability since these compounds are naturally soluble in water and therefore in the human body.

The advantage of being able to vary the composition of hydroxyapatite between 0 and 100% and that of tricalcium phosphate between 0 and 100% is that the rate of bioresorbability can be modified. This is because tricalcium phosphate is much more soluble in water than hydroxyapatite and therefore degrades more quickly in the human body. An implant wherein the TCP composition is close to 100% has relatively rapid bioresorbability compared with an implant wherein the composition is for example close to 60% hydroxyapatite and 40% tricalcium phosphate.

Preferably, the compositions of the nasal implant are indicated as a percentage with respect to the weight of each of the components. A hydroxyapatite composition of the nasal implant of between 0 and 100% indicates that the nasal implant comprises from 0 to 100% hydroxyapatite by weight.

The advantage of using hydroxyapatite is being able to benefit from its bioactive character in order to afford better tissue growth around and in the implant. The advantage of using calcium phosphates such as for example tricalcium phosphate is being able to benefit from its biodegradable and bioresorbable character. The advantage of using a composition comprising hydroxyapatite and tricalcium phosphate is obtaining a material combining bioactivity and bioresorbability properties.

Preferably, the biocompatible ceramic comprises a bioglass composition of between 0 and 100%. Preferably, the bioglass used is composed mainly of silicon oxides, sodium oxides, calcium oxides and phosphorus oxides. The bioglass is preferably used in substitution for the tricalcium phosphate. The bioglass can preferably be resorbed chemically. For example the bioglass used has a composition as a percentage by weight of 45% silicon oxides, 24.5% sodium oxides, 24.5% calcium oxides and 6% phosphorus oxides.

The advantage of using bioglass lies in its bioactivity in the presence of a living bone. In the presence of a living bone, bioglass affords a more rapid regrowth of the bone in its part exposed to the bioglass. For example, bioglass is a little more bioactive than tricalcium phosphate and is sufficiently compact.

Preferably, the density of material of said average macroporosity of the implant is between 50% and 80% and more preferentially between 60% and 75%.

Preferably, the cavities comprise openings, in that the nasal implant comprises an external surface, and in that said openings of said cavities communicate with said external surface.

The cavities are preferably pores that constitute the macroporosity. For example, the implant comprises microporosity in addition to macroporosity.

Preferably, the biocompatible ceramic further comprises a dicalcium phosphate composition of between 0 and 100%.

Preferably, the biocompatible ceramic further comprises an amorphous calcium phosphate composition of between 0 and 100%.

Preferably, the biocompatible ceramic further comprises a tetracalcium phosphate monoxide composition of between 0 and 100%.

Preferably, the tricalcium phosphate is in alpha form.
Preferably, the tricalcium phosphate is in beta form.
Preferably, the tricalcium phosphate is in gamma form.

The nasal implant may also be formed from other forms of calcium phosphate in all proportions, namely amorphous calcium phosphate (ACP), dicalcium phosphate (DCP), alpha tricalcium phosphate (α-TCP), beta tricalcium phosphate (β-TCP), gamma tricalcium phosphate (γ-TCP), pentacalcium hydroxyapatite (Hap), or tetracalcium phosphate monoxide (TCP).

The implant may preferably also comprise compounds such as calcium sulphates, calcium carbonates and for example hydroxycarbonate apatite or apatite-wollastonite.

The advantage of using one or more of these materials makes it possible to adapt the composition of the nasal implant according to the mechanical properties and bioresorbability properties sought. The advantage of using calcium phosphates with different stoichiometry and crystalline structure is being able to modify the solubility of the implant in water for example. The advantage of using calcium phosphates with different stoichiometry and crystalline structure is being able to modify the bioresorption rate.

The hydroxyapatite is preferably a pentacalcium hydroxyapatite (HAp).

Preferably, the diameters of the cavities are distributed homogeneously in the nasal implant. Preferably, the cavities are distributed periodically in the nasal implant.

Preferably, the diameters of the cavities are distributed homogeneously and periodically in the nasal implant.

Preferably, the diameters of the cavities are distributed in at least one gradient in the nasal implant.

Preferably, the average macroporosity of the return portion is higher than that of the intermediate portion.

Preferably, the cross-sections of the cavities are polygonal

Preferably, the cross-sections of the cavities are elliptical or perfectly circular.

Preferably, the cross-sections of the cavities can be inscribed in a circle.

Preferably, the cavities of the main portion are parallel to each other. Preferably, the cavities of the intermediate portion are parallel to each other. Preferably, the cavities of the return portion are parallel to each other.

Preferably, the main portion, return portion and intermediate portion are in one plane.

Preferably, the external surface is coated with a coating.

Preferably, the coating is a biocompatible material

The inventors propose, according to a second aspect of the invention, a method for manufacturing a nasal implant (5) according to the first aspect of the invention and comprising the following steps:
a. making available an additive manufacturing machine;
b. providing a program for breaking down into slices, defining a number M of layers and geometries of layers to be deposited for said nasal implant (5);
c. providing a material to be deposited comprising synthetic bioceramic;
d. depositing a layer of said material to be deposited on a support;
e. solidifying said layer;
f. repeating steps d. and e. M−1 times as defined by said breakdown program;
g. removing said material to be deposited that has not solidified;
h. carrying out a heat treatment of said printed layers in order to consolidate the remaining fraction.

The advantages of using a method using an additive manufacturing machine for manufacturing a nasal implant is being able to manufacture a nasal implant to measure. The dimensions of the nasal implant may be modified just before the manufacture of the nasal implant in order to correspond to the expectations of the patient or of the practitioner fitting the nasal implant.

The use of a 3D printing method also makes it possible to provide a nasal implant with macroporosity allowing good regrowth of the tissues in the nasal implant. 3D printing allows modification of the composition of the material to be deposited and therefore of the nasal implant without having significant modifications to be made to the 3D printer.

The 3D printing method makes it possible to manufacture a nasal implant to measure, with a made-to-measure composition and with macroporosity allowing good regrowth of the tissues and therefore good holding of the implant. The combination of the composition of the nasal implant and the macroporosity obtained by 3D printing makes it possible to have a bioresorbable nasal implant.

For example, the nasal implant is manufactured by an additive manufacturing method such as 3D printing.

Preferably, the material to be deposited comprises synthetic bioceramic and additives (polymers, photoinitiators, resins, glues).

For example, the additive manufacturing machine comprises a light source and an optical projection system.

For example, the material to be deposited has a viscosity greater than 1 Pa·s.

The advantage of using a material to be deposited having a high particle content is limiting to the maximum possible extent the shrinkage of the final piece with respect to the solidified piece. Shrinkage being in particular observed during debinding and sintering steps. The advantage of using a printing material having a high particle content is being able to obtain a dense nasal implant. The advantage of using a printing material having a high particle content is being able to obtain a nasal implant with well controlled macroporosity.

BRIEF DESCRIPTION OF THE FIGURES

These aspects as well as other aspects of the invention will be clarified in the detailed description of particular embodiments of the invention, reference being made to the drawings in the figures, in which.

The drawings in the figures are not to scale. Generally, similar elements are denoted by similar references in the figures. The presence of reference numbers in the drawings cannot be considered to be limitative, including when these numbers are indicated in the claims.

DETAILED DESCRIPTION OF CERTAIN EMBODIMENTS OF THE INVENTION

Figure 1:
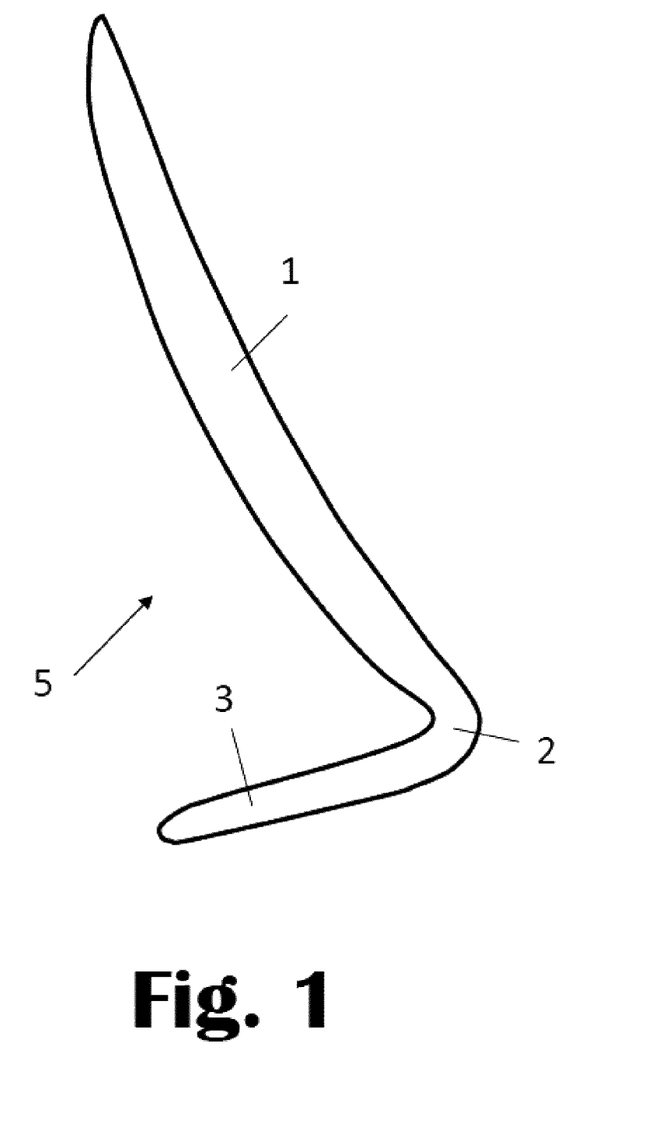
FIG. 1 shows a schematic view of a nasal implant.

FIG. 1 shows an example of an embodiment of a nasal implant 5.

The nasal implant 5 is perfectly produced by three-dimensional printing. The nasal implant 5 is for example produced by additive layer manufacturing (ALM).

The nasal implant 5 is preferably produced by three-dimensional printing with a material containing a very high concentration of particles of materials rich in hydroxyapatite and tricalcium phosphate. The nasal implant 5 is preferably subjected to chemical and heat treatments in order to eliminate any organic component. Preferably, particles of materials rich in phosphate and calcium are sintered in order to obtain a nasal implant 5 made from ceramic material.

The bioglass used in the nasal implant has for example a composition by mass of 45% silicon oxide, 24.5% sodium oxide, 24.5% calcium oxide and 6% phosphorus oxide.

The nasal implant 5 is for example obtained by machining a block. The nasal implant 5 is for example formed by an injection moulding method.

The nasal implant 5 may be produced in various sizes according to the shape of nose that a patient seeks. The nasal implant 5 may be adapted to persons of all sizes, all ages and all sexes and having individual nose shapes of very different origins. The implant 5 may be produced in order to give, for the same individual, a different nose shape. For example, the width of the nose may be chosen. For example, the angle that the nose makes with the face may be modified. For example, the angle between the bottom part of the nose and the main line of the nose may be modified. For example, the shape of the end of the nose may be adapted.

The nasal implant 5 is preferably fixed. The nasal implant 5 is for example fixed to a bone of the individual receiving the implant 5 by screws or glue. The nasal implant 5 is for example fixed to a cartilage. The nasal implant 5 may be fixed to a bone or to a cartilage. Any other combination of holding the nasal implant 5 is possible.

The nasal implant 5 has a density of material by volume preferably between 20% and 95% and even more preferably between 50% and 80%. For example, a density of 100% corresponds to a nasal implant 5 without porosity, that is to say composed entirely of ceramic material. For example a nasal implant 5 having a density of 60% by volume is composed by volume of 60% ceramic material and 40% absence of ceramic material. The absence of ceramic material corresponds to the macroporosity of the nasal implant 5.

Macroporosity is preferably present in the main portion 1, in any return portion 5 and in any intermediate portion 2. The density of material of the implant is for example higher in the intermediate portion 2 than in the main portion 1. Preferably, the density of material of the implant is adapted for each part (1, 2, 3) of the implant in order to provide optimum mechanical properties and bioabsorption properties. For example, the intermediate portion 2 requires mechanical properties that allow connection of the main portion 1 and return portion 3. For example, the intermediate portion 2 makes it possible to ensure a connection of the main portion 1 and return portion 3 so that they can begin to bioresorb while remaining in position with respect to one another.

Figure 2:
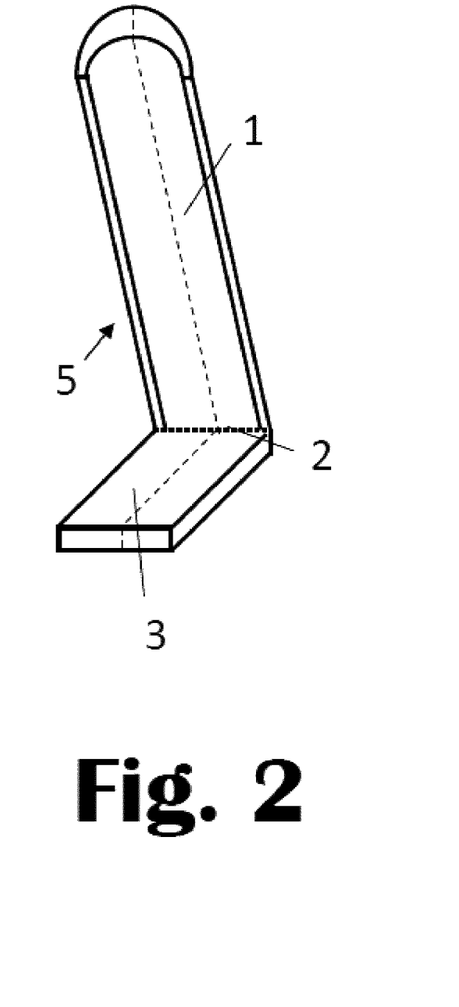
FIG. 2 shows a schematic view of a nasal implant in three dimensions.

FIG. 2 shows an example of an embodiment of a nasal implant 5. The main 1, intermediate 2 and return 3 portions are preferably in the same plane. The dashed lines represent an intersection between the nasal implant 5 and a plane. The portions 1, 2, 3 preferably extend perpendicular to said plane. For example, the parts of the main portion 1 that extend perpendicular to the plane of the implant 5 have a curvature. This curvature preferably has a center of curvature directed towards said return portion 3. The curved part of the main portion 1 makes it possible to have a nasal implant 5 that can be inserted more naturally and more harmoniously in the nose of an individual.

Preferably, the thickness of the curved part of the main portion 1 preferably varies between 0.5 mm and 10 mm. Preferably, the curved part of the main portion 1 is thinner at its ends and thicker at its center. The ends of the curved part may be defined by the parts furthest away from the central part of the main portion 1. The center of the main portion 1 is for example shown by the dashed line in FIG. 2. The radius of curvature of the curved part is preferably between 5 mm and 100 mm.

Figure 3:
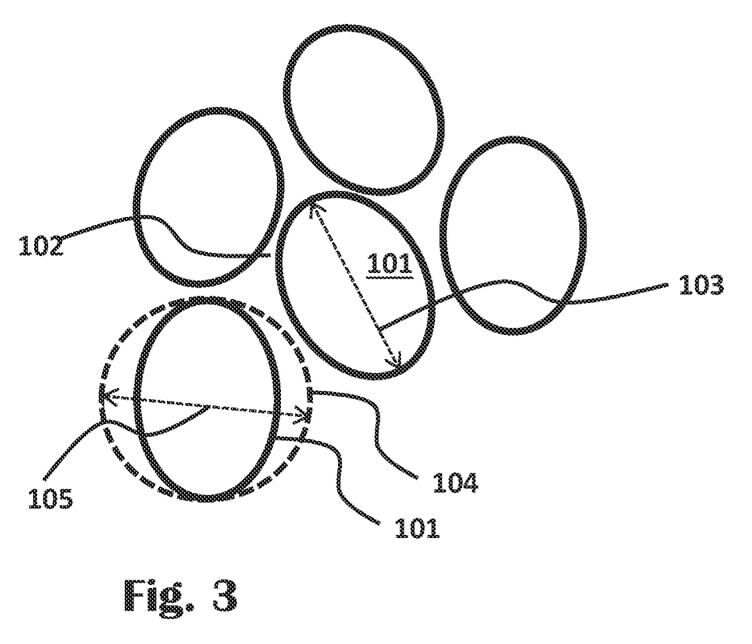
FIG. 3 shows a schematic view of a cavity.

Cavities 101 are at least partially delimited by lateral walls 102 defining sections of cavities, said sections of cavities each having an extension 103 such that it is possible to inscribe each of said sections of cavities in a circle 104 having a diameter 105 of between 0.3 mm and 1 mm (FIG. 3).

Preferably, the cavities 101 of the main portion 1 are parallel to each other. Preferably, the cavities 101 of the intermediate portion 2 are parallel to each other. Preferably, the cavities 101 of the return portion 3 are parallel to each other (FIG. 4).

Figure 4:
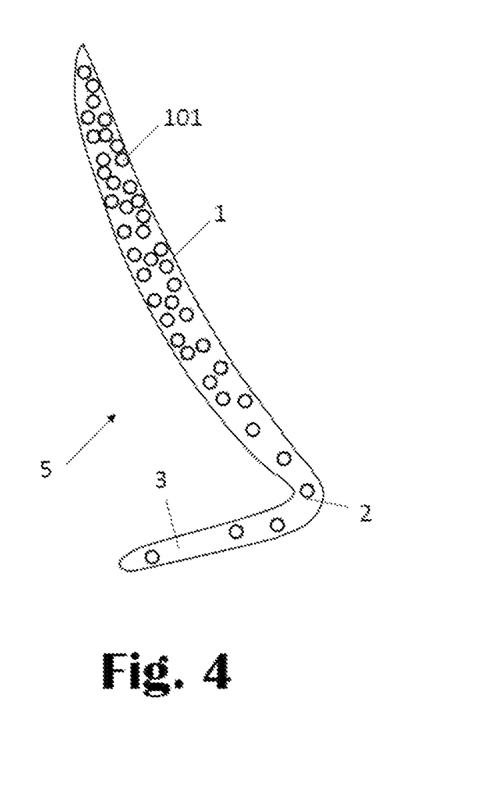
FIG. 4 shows a schematic view of a nasal implant.

Preferably, the diameters of the cavities 101 are distributed in at least one gradient in the nasal implant (FIG. 4).

Preferably, the average macroporosity of the return portion 3 is higher than that of the intermediate portion 2 (FIG. 4).

A method for manufacturing a nasal implant 5 using a 3D printing technique allows manufacture of a nasal implant 5 from a printing material. This embodiment of the invention makes provision for having a 3D printing machine making it possible to deposit the printing material in a controlled fashion. The 3D printing machine makes it possible for example to deposit uniform fine layers of the printing material. In addition, the 3D printing machine has a light source, the wavelength of which allows photopolymerisation of the printing material, and an optical projection system for exposing the printing material when it is deposited. The printing material, when it is exposed to the light source, photopolymerises by virtue of the presence of photoinitiators and monomers able to react with the photoinitiator present in the composition of the printing material.

The polymerisation of a first layer of printing material makes it possible to deposit thereon a second layer of printing material. The successive polymerisation of the layers deposited, following a clearly defined geometry for each of the layers, enables the nasal implant 5 to be manufactured.

The geometry of the layers to be printed is defined by a program of breakdown into slices. This program makes it possible for example to define the thickness of the slices that it is wished to print. The breakdown into thin slices makes it possible to obtain a better level of detail of the finished product. A breakdown into thick slices makes it possible to obtain less good details on the finished product. In choosing the number of slices in which the nasal implant is decomposed, consideration is given to the manufacturing time and the level of detail required in particular. Thicker slices require exposing the layer to the light source for longer or with the same light source delivering a greater light intensity.

The printing material preferably has a formulation very rich in inorganic material in the form of particles. The particles are preferably rich in hydroxyapatite and tricalcium phosphate. The material based on polymerisable polymer and the photoinitiator makes it possible to bind the particles of inorganic material in order to have a printing material without incorporation of air. The printing material preferably has a high viscosity, preferably of between 0.01 Pa·s and 1000 Pa·s, in order to make it possible for it to remain properly in place before and during the photopolymerisation step.

After the printing and polymerisation of the various layers, the printing material that has not been polymerised is removed from the printed object. This step is for example carried out by means of the immersion of the printed object in a solvent bath. This step is for example supplemented by heat treatment.

After the printing and polymerisation of the various layers, the particles of ceramic are preferably compacted together.

The manufacture of the nasal implant 5 by an additive manufacturing method can be carried out by stereolithography.

The manufacture of the nasal implant 5 by an additive manufacturing method may be carried out by binder jetting, that is to say by the deposition of successive layers of a binder on a powder bed. The powder bed being composed of particles of synthetic bioceramic for example.

Example of Embodiments of the Invention

A method of ceramic additive manufacturing integrates the materials, manufacturing machines and design so that:
The machine cuts the 3D file virtually into a plurality of very fine layers.
The printer next spreads a layer (25 to 100 µm) of material, and a UV source (DLP) simultaneously hardens the material.

The machine spreads a new layer on top of the first, hardens the material, and so on in order to reconstruct the object.

At the end, the object is withdrawn and the excess material is removed.

In order to obtain objects made from pure ceramic, it is necessary to eliminate the resin and to compact the powder. The parts are stoved until the resin is burnt (the debinding step). The ceramic grains are held together by very weak chemical bonds.

The increase in temperature makes it possible to fuse the grains of powder at the surface of the grains (the sintering step).

Once brought out of the oven the parts are checked for their dimensions.

The present invention has been described in relation to specific embodiments, which have a purely illustrative value and must not be considered to be limitative. In general terms, the present invention is not limited to the examples illustrated and/or described above. The use of the verbs "comprise", "include", "have", or any other variant, as well as conjugations thereof, can under no circumstances exclude the presence of elements other than those mentioned. Use of the indefinite article "a" or "an" or of the definite article "the" in order to introduce an element does not exclude the presence of a plurality of these elements. The reference numbers in the claims do not limit their scope.

In summary, the invention can also be described as follows.

Nasal implant 5 obtained by additive manufacturing, comprising a main portion 1 and a return portion 3 connected by an intermediate portion 2, the main 1 and return 3 portions forming an angle of between 25° and 90°,
  said implant is made from a biocompatible ceramic of synthetic origin;
  said implant 5 has an average macroporosity characterised by:
    a density of material of between 20% and 95% by volume, said density of material being higher in said intermediate portion 2 than in said main portion 1;
    cavities defining sections of cavities, said sections of cavities each having a diameter of between 0.3 mm and 1 mm;
  said sections of cavities each having an area and a form substantially equal over the entire implant 5.

The invention claimed is:

1. A nasal implant, comprising:
a main portion,
a return portion, and
an intermediate portion;
  said main portion and said return portion being connected by said intermediate portion;
  said main portion, said return portion and said intermediate portion including pores and being macroporous or partially macroporous,
  said main portion and return portion forming an angle of between 25° and 90°,
wherein said implant is made from a biocompatible ceramic of synthetic origin;
wherein said implant has an average macroporosity between 5% and 80%;
wherein said macroporosity is lower in said intermediate portion than in said main portion; and
wherein said pores are cavities at least partially delimited by lateral walls defining sections of cavities, said sections of cavities each having an extension such that it is possible to inscribe each of said sections of cavities in a circle having a diameter of between 0.3 mm and 1 mm.

2. The nasal implant according to claim 1, wherein said biocompatible ceramic comprises a synthetic bioceramic.

3. The nasal implant according to claim 1, wherein the biocompatible ceramic comprises a calcium phosphate composition lying between 0 and 100%.

4. The nasal implant according to claim 1, wherein the biocompatible ceramic comprises a hydroxyapatite composition lying-between 10% and 60%.

5. The nasal implant according to claim 1, wherein the biocompatible ceramic comprises a tricalcium phosphate composition lying between 40% and 90%.

6. The nasal implant according to claim 1, wherein said average macroporosity of the implant is between 20% and 50%.

7. The nasal implant according to claim 1, characterized in that the average macroporosity of the return portion is higher than that of the intermediate portion.

8. The nasal implant according to claim 1, characterized in that the cavities of the main portion are parallel to each other.

9. The nasal implant according to claim 1, characterized in that the cavities of the intermediate portion are parallel to each other.

10. The nasal implant according to claim 1, characterized in that the cavities of the return portion are parallel to each other.

11. The nasal implant according to claim 4, characterized in that the biocompatible ceramic comprises a hydroxyapatite composition lying between 25% and 45%.

12. The nasal implant according to claim 5, characterized in that the biocompatible ceramic comprises a tricalcium phosphate composition lying between 55% and 75%.

13. The nasal implant according to claim 6, characterized in that said density of material of said average macroporosity of the implant is between 60% and 75%.

14. A nasal implant, comprising:
a main portion,
a return portion, and
an intermediate portion;
  said main portion and said return portion being connected by said intermediate portion;
  said main portion and return portion forming an angle of between 25° and 90°,
wherein:
  said implant is made from a biocompatible ceramic of synthetic origin; and wherein
  said implant has an average macroporosity between 5% and 80%;
  said macroporosity is lower in said intermediate portion than in said main portion;
  wherein pores are cavities at least partially delimited by lateral walls defining sections of cavities, said sections of cavities each having an extension such that it is possible to inscribe each of said sections of cavities in a circle having a diameter of between 0.3 mm and 1 mm;
  wherein porosity of the implant is connected such that a route exists between the pores over whole of the implant without passing outside the implant.

15. A nasal implant, comprising:
a main portion,
a return portion, and
an intermediate portion;

said main portion and said return portion being connected by said intermediate portion;

said main portion and return portion forming an angle of between 25° and 90°, wherein:

said implant is made from a biocompatible ceramic of synthetic origin; and wherein said implant has an average macroporosity between 5% and 80%;

said macroporosity is lower in said intermediate portion than in said main portion;

wherein the pores are cavities at least partially delimited by lateral walls defining sections of cavities, said sections of cavities each having an extension such that it is possible to inscribe each of said sections of cavities in a circle having a diameter of between 0.3 mm and 1 mm; and wherein average macroporosity of the return portion is greater than that of the intermediate portion.

* * * * *